(12) United States Patent
Cinti

(10) Patent No.: US 8,926,036 B2
(45) Date of Patent: Jan. 6, 2015

(54) APPARATUS FOR MARKING HISTOLOGY EMBEDDING CASSETTES

(76) Inventor: Mario Cinti, Ascoli Piceno (IT)

( * ) Notice: Subject to any disclaimer, the term of this patent is extended or adjusted under 35 U.S.C. 154(b) by 0 days.

(21) Appl. No.: 14/115,216

(22) PCT Filed: Mar. 24, 2012

(86) PCT No.: PCT/EP2012/002226
§ 371 (c)(1),
(2), (4) Date: Nov. 1, 2013

(87) PCT Pub. No.: WO2012/159762
PCT Pub. Date: Nov. 29, 2012

(65) Prior Publication Data
US 2014/0071190 A1    Mar. 13, 2014

(30) Foreign Application Priority Data

May 26, 2011 (IT) .............................. BO2011A0304

(51) Int. Cl.
| | |
|---|---|
| *B41J 3/00* | (2006.01) |
| *B41J 2/01* | (2006.01) |
| *B05C 11/00* | (2006.01) |
| *B05D 3/00* | (2006.01) |
| *B05D 5/00* | (2006.01) |
| *B41J 3/407* | (2006.01) |
| *B01L 3/00* | (2006.01) |
| *G01N 35/00* | (2006.01) |

(52) U.S. Cl.
CPC .............. *B41J 3/4073* (2013.01); *B01L 3/545* (2013.01); *G01N 35/00732* (2013.01); *G01N 35/0099* (2013.01); *B01L 2200/025* (2013.01); *B01L 2300/021* (2013.01); *G01N 2035/0089* (2013.01); *G01N 2035/00831* (2013.01)

USPC .......... 347/2; 347/1; 347/4; 118/46; 427/2.11; 427/258

(58) Field of Classification Search
USPC ........ 347/1, 2, 4; 435/283.1, 287.1; 427/2.11, 427/258; 118/46
See application file for complete search history.

(56) References Cited

U.S. PATENT DOCUMENTS

| | | |
|---|---|---|
| 6,518,542 B1 | 2/2003 | Robertson et al. |
| 6,615,763 B2 * | 9/2003 | Edwards .......................... 118/46 |

(Continued)

FOREIGN PATENT DOCUMENTS

| | | |
|---|---|---|
| EP | 2159562 A2 | 3/2010 |
| WO | 2008068525 A1 | 6/2008 |

OTHER PUBLICATIONS

International Search Report for corresponding International Application No. PCT/EP2012/002226.

*Primary Examiner* — Jannelle M Lebron
(74) *Attorney, Agent, or Firm* — Egbert Law Offices, PLLC

(57) ABSTRACT

A marking apparatus for marking histology embedding cassettes includes a marking device for marking plastic surfaces, a gripping means to grip and release a cassette, and a movement organ to rotate the gripping means with respect to a first rotation axis perpendicular to a second rotation axis. The first axis is arranged such that it is situated in an ideal plane that is parallel to and interposed between the ideal planes in which the perpendicular surfaces of a cassette, gripped by the gripping means, are located, so that, upon rotation with respect to the first axis the first and the second perpendicular surfaces can alternately be located in front of the marking device. The second axis being arranged with respect to the gripping means such that, upon rotation with respect to the second axis, the oblique surface of the cassette can be in front of the marking device.

14 Claims, 11 Drawing Sheets

(56) References Cited

U.S. PATENT DOCUMENTS

| | | |
|---|---|---|
| 2003/0049178 A1 | 3/2003 | Kiene et al. |
| 2008/0194016 A1 | 8/2008 | Kusters |
| 2009/0210254 A1 | 8/2009 | Gurney |
| 2013/0222444 A1 * | 8/2013 | Cummins et al. .................. 347/4 |

\* cited by examiner

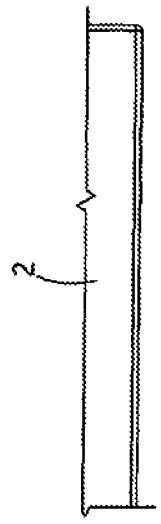
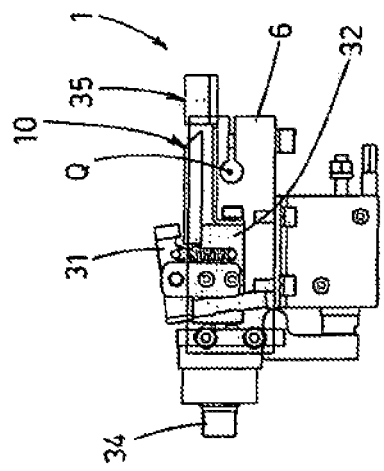
FIG.1
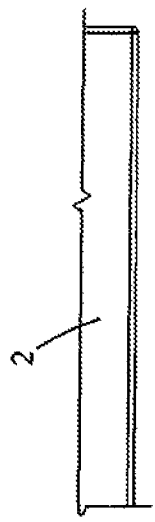
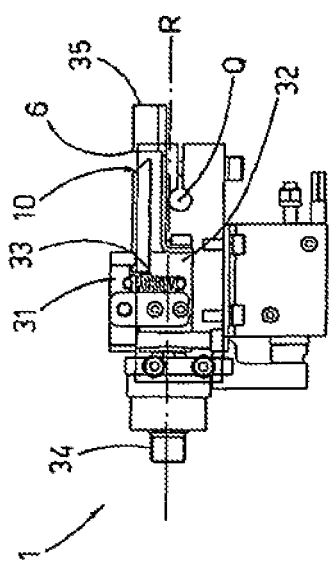
FIG.2

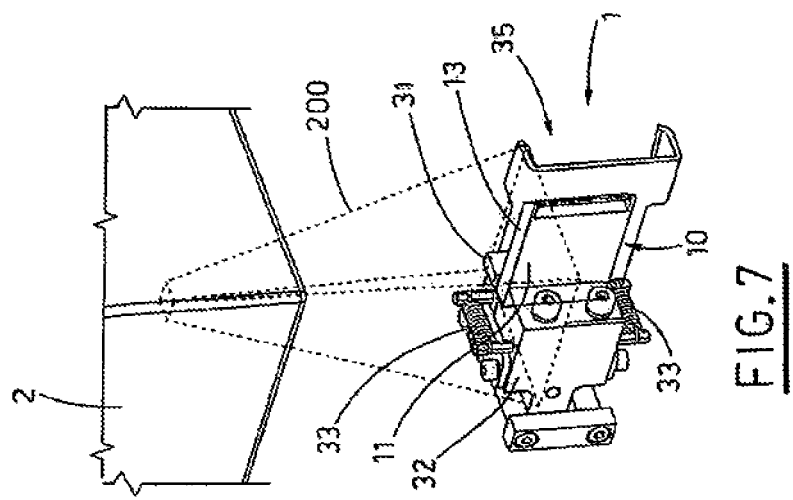
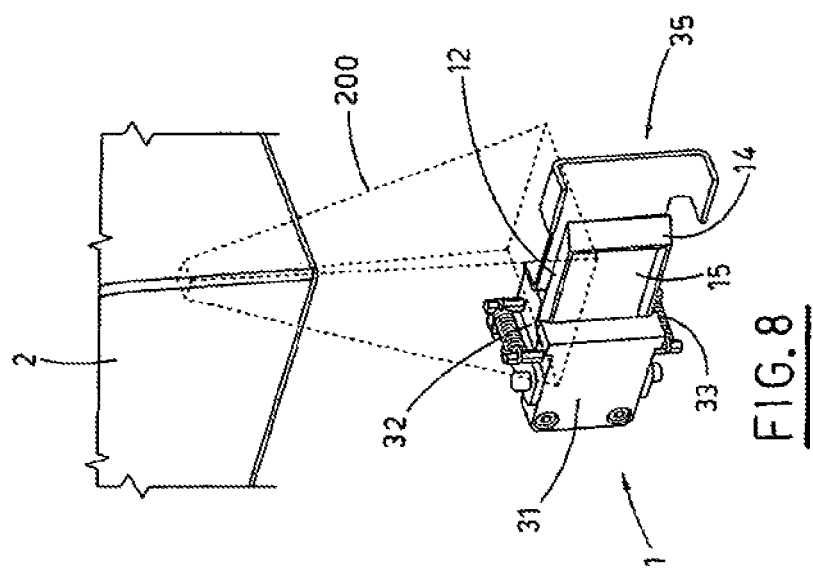

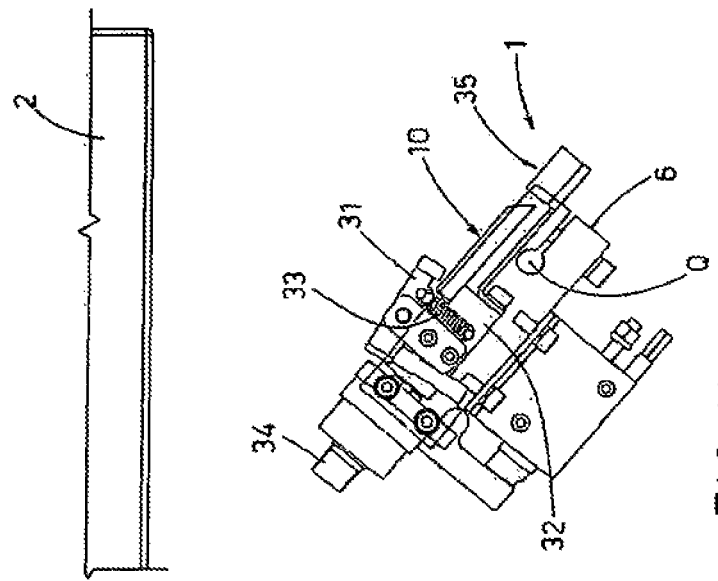
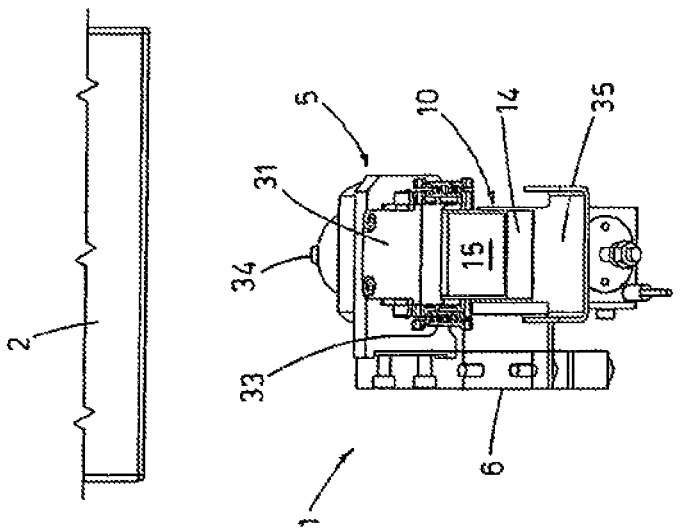

APPARATUS FOR MARKING HISTOLOGY EMBEDDING CASSETTES

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present inventions relates to surface marking devices.

In detail, the invention concerns devices for high contrast marking of exposed surfaces of histology embedding cassettes.

2. Description of Related Art Including Information Disclosed Under 37 CFR 1.97 and 37 CFR 1.98.

Embedding cassettes are healthcare consumables commonly used in analysis laboratories and hospitals.

They have the shape of a box and are envisaged to contain and hold tissue specimen for histology or cytology tests.

They are available in different sizes; the larger cassettes are used to contain larger specimens and in medical jargon they are called mega-cassettes and "supermega" cassettes.

Basically a common embedding cassette comprises a main containment unit and a cover (sometimes of the removable type).

The main unit of the embedding cassette, usually made of plastic material, comprises a rectangular base with sides that depart from its perimeter, defining the space to house the specimen.

The cover closes the specimen in the housing.

One of the sides, practically one side of the said cassette, has an oblique surface for the marking.

Each cassette in fact, must be marked with identification details of the patient from which the specimen is collected, of the hospital ward in which the patient is hospitalized on the date of the specimen collection, and any other information, so that this information can be associated to the results of the specimen analyses.

The oblique surface of the cassettes is often marked by hand using special pens or felt tips, by the operators in charge of the analysis.

This type of marking presents some drawbacks.

First of all the correctness and intelligibility of the writing vary according to the person that marks the cassettes, because they depend on individual competences and skills.

Furthermore, barcodes cannot be handwritten (traditional or bidimensional, such as Data Matrix ones).

An attempt to overcome these drawbacks is made by adopting automatic ink-jet printing devices, specially designed for marking the oblique surface of the histology embedding cassettes.

These printing devices can mark the cassettes with barcodes and perform markings of a uniform quality; there are however maintenance problems and problems related to the calibration of the printing heads.

Use in analysis laboratories has shown that markings performed with these printing devices on the oblique surface of a cassette, especially in the case of small ones, but not only, are so cramped that they often cannot even be read by optical barcode readers, etc.

Furthermore, as the size of the oblique surface represents a limit to the amount of useful information than can be printed on the cassette, known printing devices can only print a very limited amount of useful information. US 2003/0049178 A1 discloses a marking apparatus for marking cassettes made of plastic, comprising a printing head suitable for marking plastic surfaces presented before it and gripping means able to alternatively gripping and releasing an embedding cassette. The printing head can be rotated with respect to one rotation axis in such a way that it can only face the oblique surface of the cassette, not also the side-walls of the cassette adjacent to the oblique wall.

SUMMARY OF THE INVENTION

The object of the present invention is to overcome these and other drawbacks by making available a marking apparatus for marking histology embedding cassettes made of plastic material, in conformity with claim 1.

Please note that an embedding cassette comprises a flat base, a first and a second external side opposite each other, having respectively a first and a second flat surface, perpendicular to the flat base and parallel to one another, and further comprises a third external side having a flat oblique surface.

The apparatus proposed comprises:
at least a marking device suitable for marking plastic surfaces presented before it;
at least a gripping means able to alternatively grip and release an embedding cassette; and
a movement organ to rotate the gripping means with respect to at least a first rotation axis and at least a second rotation axis.

According to an essential aspect of the invention, the first rotation axis is arranged with respect to the gripping means in such a way that, in use, the first rotation axis is situated in an ideal plane that is parallel to and interposed between the ideal planes in which the perpendicular surfaces of a cassette, gripped by the gripping means, are located, so that, upon rotation of the gripping means with respect to the first axis, the first and the second perpendicular surfaces, can alternately be located in front of the marking device.

A further essential aspect is that the second rotation axis is perpendicular to the first rotation axis and is arranged with respect to the gripping means in such a way that, in use, upon rotation of the gripping means, with respect to the second axis, the oblique surface of the gripped cassette can be in front of the marking device.

Given that the proposed apparatus includes the movement organs of the gripping means, configured to define the rotation axes as explained above, it is capable of marking not only the oblique surface of the cassettes but also the two perpendicular sides, so that more information can be marked compared to the known technique and/or the information marked is more intelligible for the human eye and for automatic readers.

Furthermore, the invention can write any type of symbol or graphic code, such as bar codes and Data matrix codes on the three surfaces of the cassette, with a muniform quality and without any lapsus calami.

The invention therefore overcomes all the drawbacks of the known technique. The marking device can be, by way of a non-limiting example, of the heat transfer (i.e. that adopts the known dye-sublimation technology), ink-jet type or, preferably, of the laser type.

Advantageously, when the marking device is of the laser type, then the invention can permanently mark the histology embedding cassettes.

It is in fact know that once the specimen is housed in the cassettes, they are subjected to chemical agents used to analyse the specimen (the rectangular base, and at times the cover, are perforated).

It is common experience, that the said chemical agents may at times delete the information marked using ink, or make it illegible; at present inks that are completely indelible when subjected to the chemical agents concerned have not yet been conceived.

Furthermore, laser technology can mark plastic surfaces with a very high contrast, to the advantage of the legibility of the writing.

In this way, even cassettes with surfaces of the most varied colours can be marked.

BRIEF DESCRIPTION OF THE SEVERAL VIEWS OF THE DRAWINGS

The invention will now be better illustrated by means of a detailed description of embodiments and advantageous technical-functional characteristics related to the said embodiment, which can be derived in part by the above mentioned description, according to what is specified in the claims, and with the help of the accompanying drawings, in which:

FIGS. 1 and 2 show the side views of the apparatus of the invention in an operating phase while gripping a histology embedding cassette;

FIGS. 7 and 8 show axonometric views of the apparatus in the operating phases of the previous two figures;

FIGS. 11 and 12 show a side view and front view of the apparatus, respectively, in the cassette releasing phase;

Figure 3:
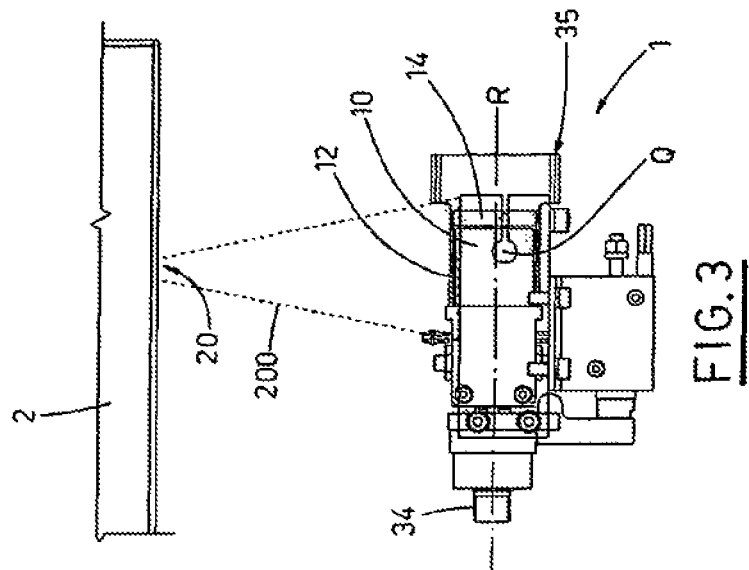
FIGS. 3 and 5 show the side views of the apparatus in different marking phases.
Figure 4:
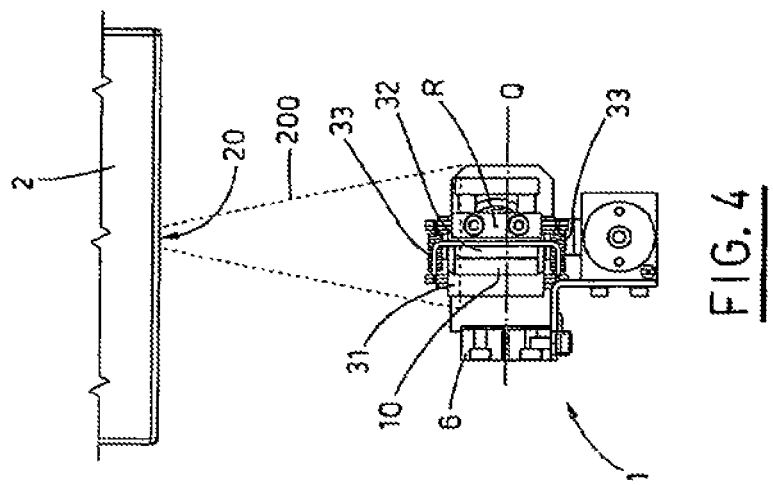
FIGS. 4 and 6 show front views of the apparatus in the operating phases of the previous two figures.
Figure 5:
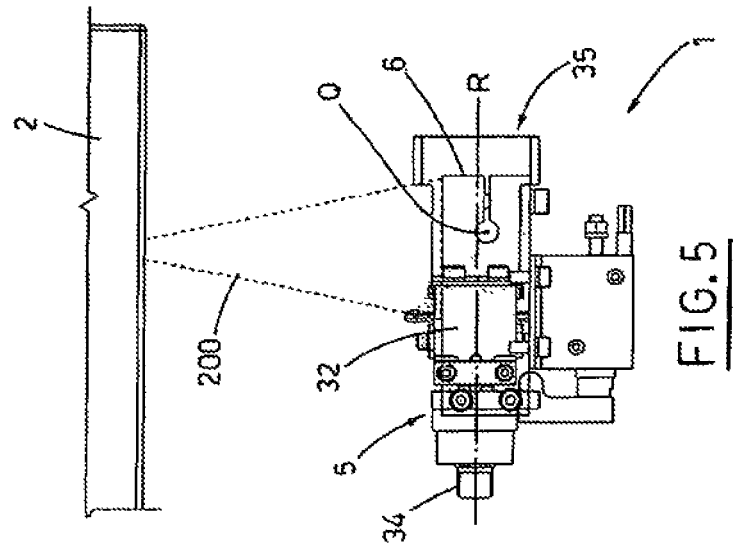
Figure 6:
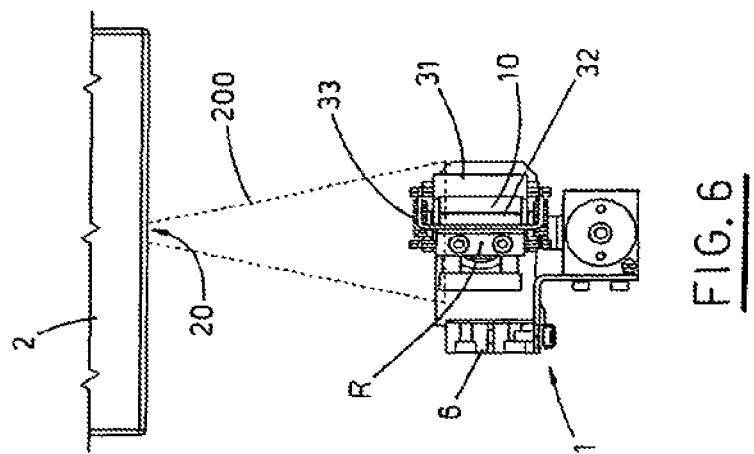

FIGS. from 15 to 22 show details of the machine in the two previous figures, represented with axonometric views.

In the enclosed figures, 11 denotes the marking apparatus proposed, as a whole, in its preferred version, in which it comprises a marking device 2, which is of the laser type.

DETAILED DESCRIPTION OF THE INVENTION

Please note that, in general, apparatus 1 envisages: the laser marking device 2 having an outlet 20; the gripping means 31, 32 arranged in front of the outlet 20 of the marking device 2; the movement organ 5, 6, 7 to rotate the gripping means with respect to the first or second rotation axis R, Q.

Before describing in detail the construction and functional aspects of the invention, please note that an example of histology embedding cassette 10, for which the invention can be used, has a box shape with a lower rectangular base 11 from which depart four sides that internally define a housing 15 for the specimen, and externally define the four sides of the cassette 10.

The four sides include a first and a second side opposite each other having respectively, surfaces 12, 13 perpendicular to the base 11 and parallel to one another, and a third side having an oblique surface 14.

In detail, the oblique surface 14 is arranged on the front external side of the cassette 10, and the perpendicular surfaces 12, 13 originate from its shorter sides; the perpendicular surfaces 12, 13 are arranged on those external sides that define the sides of the embedding cassette 10.

In the figures enclosed, we have chosen to show, by way of example, a cassette 10 of the type with a removable cover, and in detail, it is shown in all the figures with the cover removed.

In practice, it is assumed that the apparatus 1 supplies as output cassettes 10 already marked, with a housing 15 in which the operator will place the specimen to be analysed; the operator will then close the specimen in the cassette 10 using a cover (not shown) which is available separately.

The apparatus 1 however, works perfectly even with cassettes 10 closed by the cover, and which must therefore be opened to insert the specimen, independently from whether the cover is removable or not.

In the case of a cassette 10 without cover, it shall present a portion 16 opposite the base 11 comprising the uncovered upper edge of the above mentioned sides.

The invention envisages the configuration of the movement organs of the gripping means 31, 32 in relation to the dimension of the cassette 10.

In practice this means that the arrangement of the rotation axes R, Q, with respect to which the gripping means 31, 32 moves, is in relation to the dimension of the cassette 10 and of the inclination of the oblique surface 14.

Please note also, that from a general point of view, there are two conditions that must be satisfied by the rotation axes R, Q in order to alternately mark the three surfaces 12, 13, 14 concerned.

The first condition is that the first rotation axis R is arranged with respect to the gripping means 31, 32 so that, in use, it is in an ideal plane that is parallel and interposed between the ideal planes in which the perpendicular surfaces 12, 13 of the gripped cassette 10 are located (see FIGS. from 1 to 12).

The second condition is that the second rotation axis Q is perpendicular to the first rotation axis R and is arranged with respect to the gripping means 31, 32 in such a way that, in use, i.e. during the marking phase, upon rotation of the gripping means 31, 32, with respect to the second axis Q, the oblique surface 14 of the gripped cassette 10 can be in front of outlet 20 of the marking device 2.

Particular cases of these general conditions will be detailed later, in the description of how the invention works.

Before the explanation of the operation of the invention, please find below some preferred structural aspects.

As can be seen in the figures enclosed, the gripping means comprises gripping pliers with two jaws 31, 32, which are openable to receive one cassette 10 at a time and closeable to grip the cassette 10.

The said jaws 31, 32, as clearly shown in the figures, are suitable for engaging the flat base 11 of the cassette 10 and the above mentioned upper portion 15 thereof, leaving the first and second perpendicular surfaces 12, 13 and the oblique surface 14 thereof uncovered; in this way the said surfaces are directly accessible, i.e. exposed, to the laser emissions (pulses or rays) produced by the marking device 2.

In a preferred embodiment, the laser marking device 2 is arranged above the gripping pliers 31, 32, which are below the emission outlet 20 of device 2.

Before examining other construction details, please find below a description of the preferred operating mode of the invention, as defined in one of its embodiments.

Figure 18:
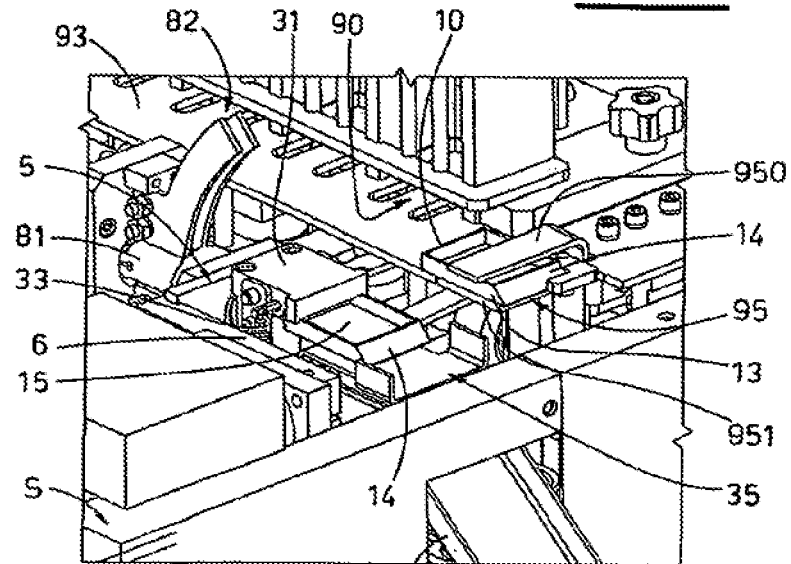
Figure 19:
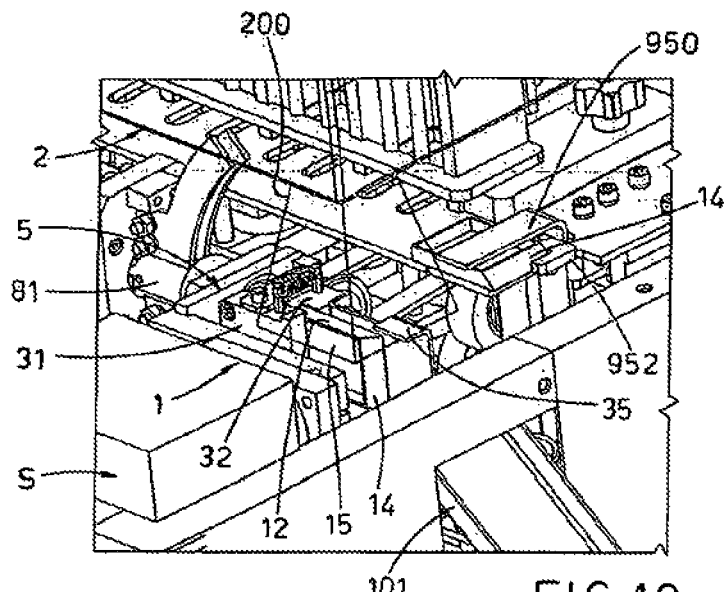
Figure 20:
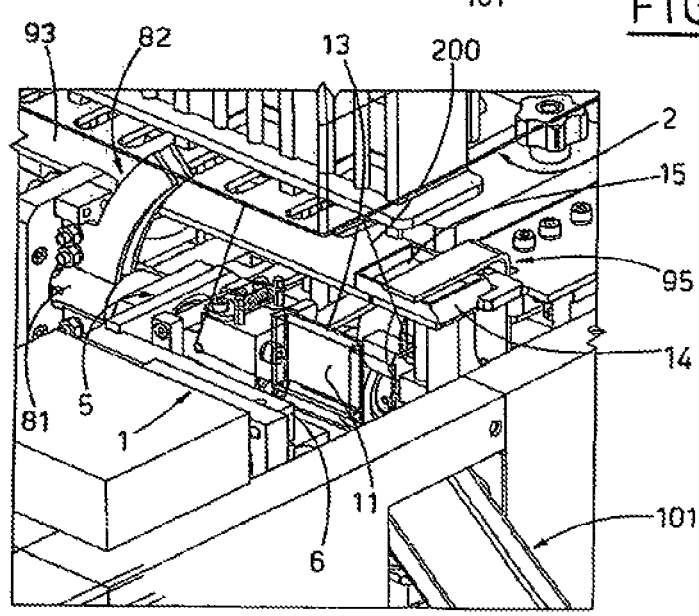
Figure 21:
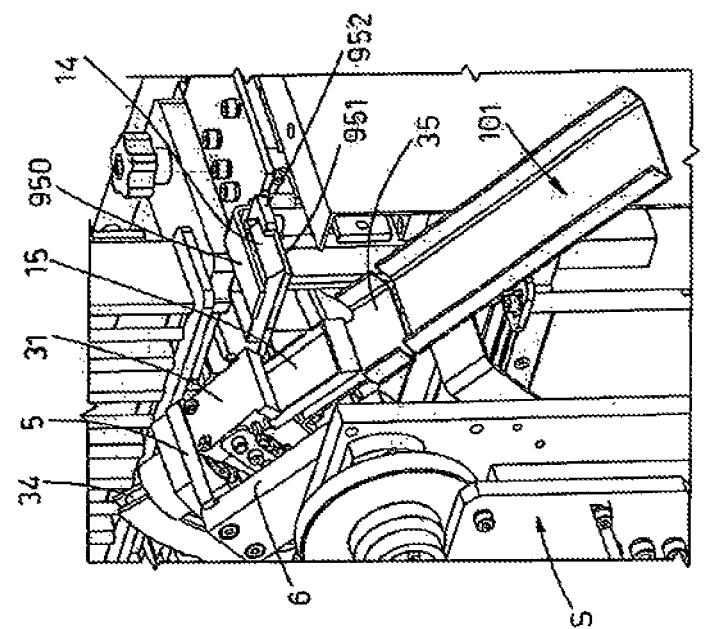
Figure 22:
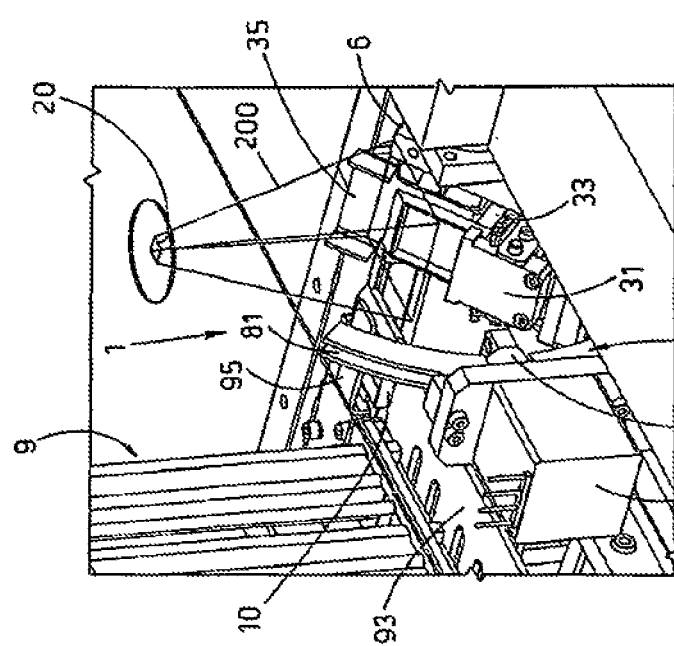

In the loading phase, shown in FIGS. 1, 2 and 18 the gripping pliers 31, 32 are arranged in an intermediate position in which the jaws 31, 32 are one above the other.

In this phase the cassette 10 is presented horizontally to the gripping pliers 31, 32 when they are open, as shown in FIG. 1 the gripping pliers then close to tightly grip the cassette 10, keeping it horizontal, as shown in FIG. 2.

Then, in the first marking phase the gripping pliers 31, 32 are rotated by ninety degrees with respect to the first rotation axis, so they are arranged in the first semi-tilted position, as shown in FIGS. 3, 4, 8 and 19; the first perpendicular surface 12 of the gripped cassette 10 is horizontal and directly facing the outlet 20 of the laser marking device 2.

in this phase the laser marking device 2 is operated to write on the first perpendicular surface.

The laser marking device 2 is of the preferred type that engraves the surface of the cassette 10 with high contrast positive marking.

Please note that 200 denotes the schematic representation of the operating cone of the laser device 2, i.e. the space in which the device 2 can write.

As shown in the figures, the gripping pliers 31, 32 are arranged with respect to the output 20 of the device 2 so that in the writing phases the cassette 10 is always positioned within the operating cone of the device 2.

During the second writing phase, see FIGS. 5, 6, 7 and 20, the gripping pliers 31, 32 are rotated by one hundred and eighty degrees with respect to the first semi-tilted position, so they are arranged in a second semi-tilted position, in which the second perpendicular surface 13 of the gripped cassette 10 is horizontal and directly facing the outlet 20 of the marking device 2, which can therefore mark the envisaged writing.

To prepare the third writing phase the gripping pliers 31, 32 are once again placed in the intermediate position by rotating them ninety degrees with respect to the first rotation axis R (see FIG. 2 again).

Figure 9:
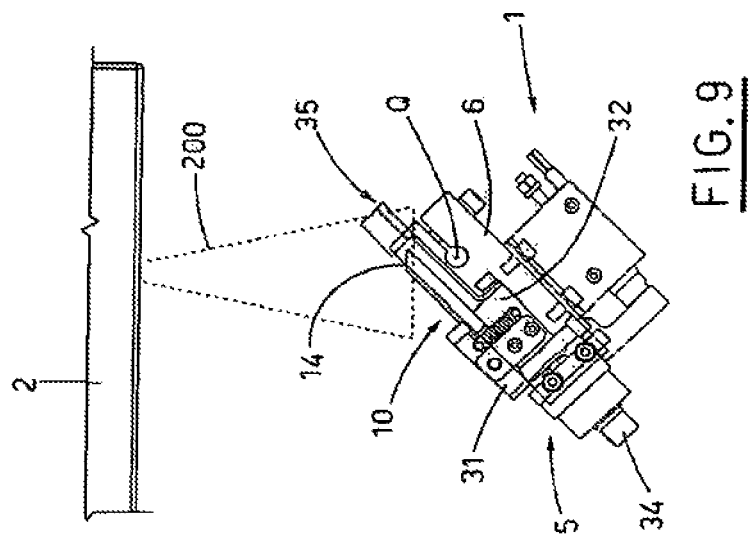
FIGS. 9 and 10 show a side view and front view of the apparatus, respectively, in the marking phase of the front oblique surface of a cassette.
Figure 10:
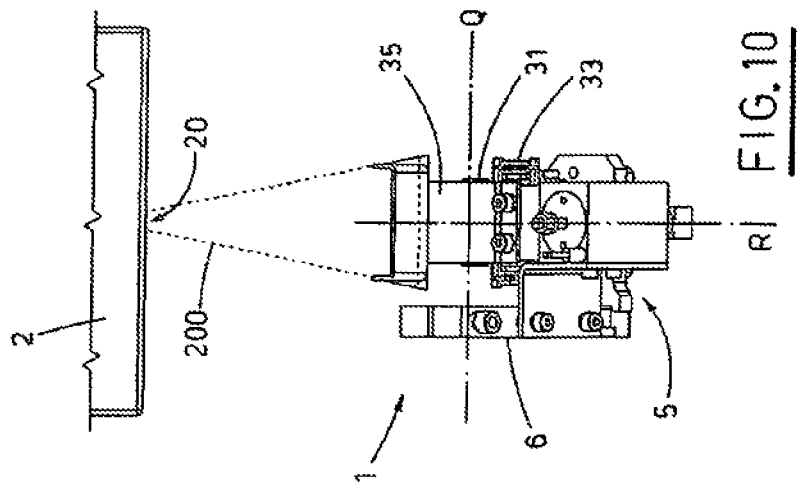
Figure 13:
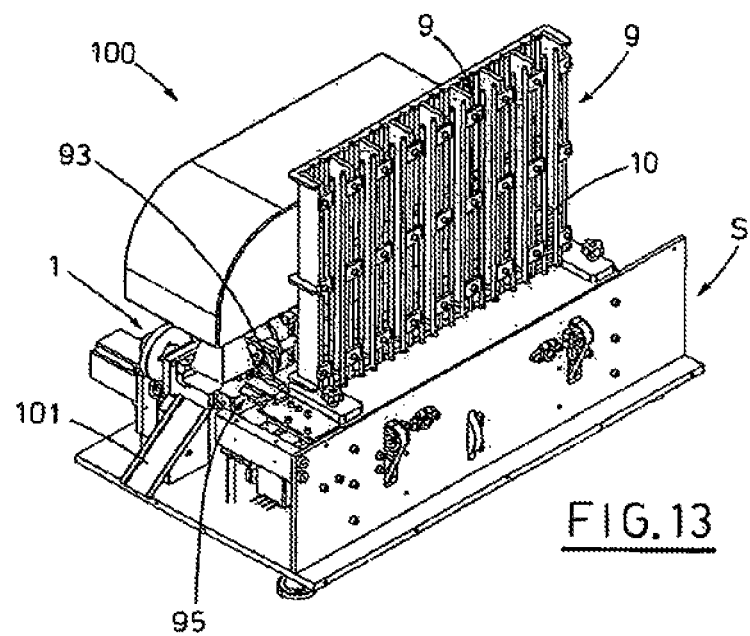
FIGS. 13 and 14 show an axonometric view and a view from the top of a machine that supplies marked cassettes, that comprises an apparatus according to the invention.
Figure 14:
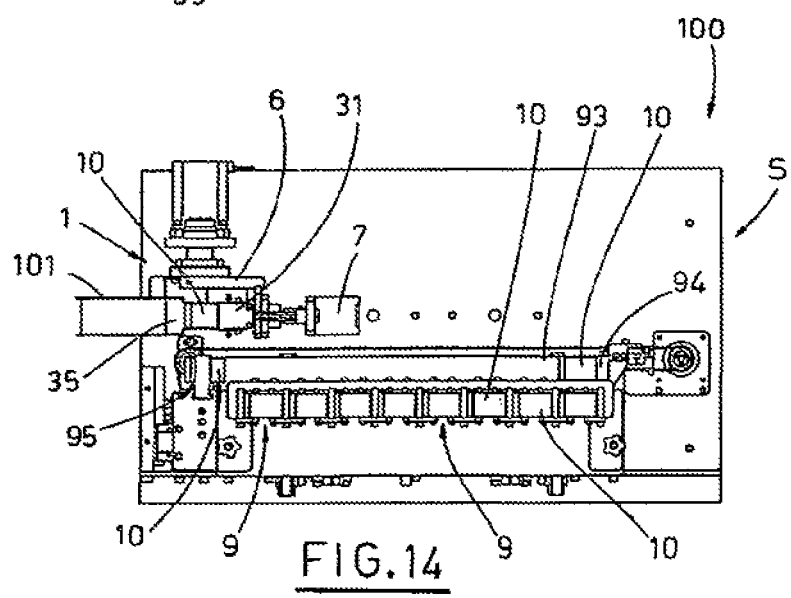
Figure 15:
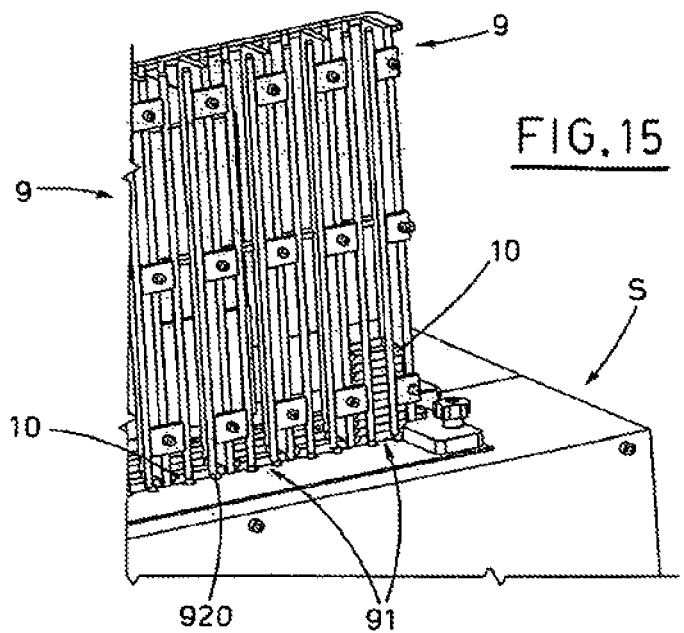

In the following third writing phase the gripping pliers are arranged, following a rotation with respect to the second rotation axis Q, in a pitched position in which the gripped cassette 10 is arranged obliquely with respect to the direction of gravity and the oblique surface 14 is horizontal and is directly facing the outlet 20 of the marking device 2 (see FIGS. 9 and 10).

In this phase, obviously, the front part of the cassette 10, and therefore its oblique surface 14, is lifted during the above mentioned rotation.

At this point, always in the third writing phase, the marking device 2 writes on the oblique surface 14 of the cassette 10 the envisaged identification details, etc. . . .

At this point the marked cassette 10 is made available to the operator thanks to the release phase illustrated in FIGS. 11 and 12.

In this phase the gripping pliers 31, 32, together with the gripped cassette 10 are first of all rotated once again with respect to the second axis Q, but in the opposite direction of the previous phase, so that the gripping pliers 31, 32 are arranged in a release position in which the cassette 10 is tilted with respect to the vertical axis, but has the front part facing downwards.

As shown in FIGS. 11 and 12, the gripping pliers 31, 32 are then opened and the marked cassette is released and exits the apparatus 1 by gravity.

According to alternative operating modes, the above mentioned phases can be carried out in different sequences or some phases can be skipped, for example if only the oblique surface 14 of the cassette 10 needs to be marked with identification details (in this case it is not necessary to carry out the rotations with respect to the first axis R, and any related operation).

The apparatus 1 proposed is obviously controlled automatically by an electronic processor connected to the marking device 2, to the movement organ 5, 6, 7 of the gripping pliers 31, 32, and to the gripping pliers so that they operate in phase.

When the surfaces to be marked 12, 13, 14 are, each time and alternately, placed facing the outlet 20 of the marking device 2 to be marked, they are preferably arranged in the same ideal plane.

This is preferably obtained by choosing, according to the dimensions of the cassettes 10 to be marked and to trigonometric calculations, the arrangement of the two rotation axes R, Q with respect to one another.

In detail, the first and the second rotation axes R, Q are arranged with respect to one another in such a way that, in use, upon rotations of the gripping pliers 31, 32 (or other suitable gripping means), with respect to the first and/or second rotation axes R, Q, the first perpendicular surface 12, the second perpendicular surface 13 and the oblique surface 14 are alternately arranged in the same ideal plane.

In this way a high level of uniformity and contrast effectiveness is guaranteed because the surfaces to be marked are always in the same plane and therefore they receive the same laser emission power, notwithstanding irrelevant deviations and fluctuations.

In fact, in practice, with this solution the ideal plane in which the surfaces to be marked are arranged each time, can be a parallel plane at a fixed distance from the focal plane (i.e. a plane that is perpendicular to the focal axis).

Therefore when the surfaces 12, 13, 14 are marked, they are always at the same distance from the focal plane and do not present casual tilted positions.

Consequently, the calculations for the best position of the cassette 10 in order to obtain good quality marking are made easier, as well as the operations to set the marking device 2; the settings remain unchanged for a given type of cassette 10 to be marked.

An alternative operating mode will be illustrated later in the description of a particular variation of the invention.

Please find below possible particular structural aspects of the invention.

Preferably, the jaws are two shaped blocks 31, 32, for example made of plastic material, hinged to each other and connected by elastic return means 33 (e.g. springs), the said blocks 31, 32 being opened by the pressure exercised by a pressor (not illustrated) included in the gripping means of the invention (practically it can be included in the component called "gripping pliers" in this description).

The pressor is a small actuator, which can be connected to the electronic processor, incorporated in the jaws 31, 32, comprising a sliding stem than can be operated alternately to press one of the blocks 31, 32 or to withdraw itself. In practice, one of the blocks 32 is fixed and the other block 31 rotates with respect to the former one, with a mandible-like movement (like the jaw of an alligator), following the pressure exercised by the pressor stem on the rotating block 31 in a point which can be easily defined by an expert in this sector. The movement organ 5, 6, 7 of the gripping pliers 31, 32 can be constructed as follows (see FIGS. 18 to 22).

First of all it can envisage a frame to support the gripping pliers 31, 32, generally indicated in the figures as 5, which is fixed rigidly to an end of a tilting arm 6, the latter being hinged (in the manner later described) about the rotation axis Q.

The tilting arm 6 is connected, directly or by means of driving gears, to a special motor that rotates it with respect to the second rotation axis Q, in order to perform the rotations of the gripping pliers 31, 32 with respect to the second rotation axis, with the aim of marking for example the oblique surface 14 of a gripped cassette 10.

Therefore, the mutual arrangement of the second rotation axis Q and the gripping pliers 31, 32 and of the second rotation axis Q and the first rotation axis R depend on the length of the rotation arm 6.

The frame 5 that supports the gripping pliers 31, 32 and therefore the cassette 10 which is gripped each time, can be in turn supported by the arm itself 6, supported by a small bench, or as we will see, by the support structure of a machine 100 of which the apparatus 1 proposed is a sub-unit.

The gripping pliers 31, 32 are coupled in a rotary fashion to the frame 5 so they can rotate with respect to the first rotation axis R.

A possible solution to rotate the gripping pliers 31, 32 about the first axis R is described below.

A first driving motor 7 with the task of generating the rotation with respect to the first axis R can be envisaged to be fixed, and not mounted on the frame 5, with respect to the rotations of the latter with respect to the second axis Q. In practice, the back of the gripping pliers 31, 32 incorporates an engagement tang 34 suitable to be engaged by the first motor mentioned 7, to produce the rotation; the said tang 34 juts out the back of the frame 5 that supports the gripping pliers 31, 32.

The tang 34 may have a flat end, in which case, to ensure that the gripping pliers 31, 32 do not rotate in an unwanted manner with respect to the first axis R, when the former is rotated with respect to the second axis Q, and in any case when the tang 34 is not engaged by the first motor, a special restricting structure 8 can be installed between the motor 7 and the frame 5.

The structure 8 comprises a tube 81, placed directly in front of the motor 7, with an internal cylindrical space sufficient to allow for the free rotation of the tang 34 when engaged by the motor.

The structure 8 also comprises an upper pair and a lower pair of arched plates with two sides 82, 83 positioned at a mutual distance so as to create an upper passage and a lower passage that communicate with the space inside the tube 81; the said passages constitute an anti-rotation restriction for the tang 34, when its flat section is interposed between them, which occurs upon rotation of the gripping pliers with respect to the second rotation axis Q.

The profile of the arched plates is that of circular arcs having as centre a respective point placed on the second rotation axis Q.

In practice the distance of the plates of each pair is slightly greater than the thickness of the flat section of the tang 34.

According to an alternative embodiment of the inventions (not shown in the figures), which has its own characteristic operating mode, all the marking results of the phases described above, and also the coplanarity of the surfaces 12, 13, 14 while they are being marked, can be obtained by envisaging that the movement organ comprises a second motor directly connected either to the gripping pliers 31, 32 or to the frame 5, instead of comprising the rotation arm 6, and that it also comprises a linear actuator connected to the gripping pliers 31, 32 or to the frame.

In practice, in this version, the second rotation axis Q goes near the gripping pliers 31, 32 and in the writing phase of the oblique surface 14, the rotation with respect to the second axis Q only has the task of positioning the oblique surface 14 horizontal; the arrangement of the gripping pliers in the same ideal plane mentioned above, in which the perpendicular surfaces 12, 13 are placed during the writing phase, is controlled by the linear actuator.

The next part describes a machine 100 that supplies already-marked histology embedding cassettes, of which the apparatus 1 proposed, is a sub-unit.

The machine 100 must comprise, in the most general configuration and layout: a marking apparatus 1; a plurality of linear or circular stores 9, to retain a multiplicity of embedding cassettes 10; conveyor means 93, 94, 95 to supply one cassette 10 at a time to the marking apparatus 1, arranged between the stores 9 and the marking apparatus 1; and at least an outlet 101 to provide an operator with a marked histology embedding cassette 10.

The various units of the machine 100, including the apparatus 1, are supported by a support structure generally denoted by slim elements, so that in practice the machine 100 can rest on a table or a worktop in the analysis laboratory.

The next section explains how these units of the machine 100 can be realised, in particular with reference to FIGS. from 13 to 22.

Each store 9 is able to contain a vertical stack of cassettes 10 that can slide vertically, for example enclosed between plates and/or vertical rods, which in practice define the stores 9.

The store 9 comprises a lower rest base to support the stack of cassettes 10, and an outlet opening 90, of a size which is sufficient for the passage of a cassette 10, the opening 90 being arranged at the base, for example on the side.

When the store 9 is loaded with the stack of cassettes 10, the outlet opening 90 faces directly the cassette 10 at the bottom of the stack, i.e. the cassette 10 that rests directly on the base.

Each store 9 also has an access passage 91, which is opposite the outlet opening 90, by means of which the cassette 10 at the bottom of the stack is directly accessible from outside.

Preferably, the cassettes in the stack have the base 11 facing downwards, and when they rest directly on the base of the store 9, they have the first perpendicular surface 12 facing the access passage 91 and the second perpendicular surface 13 facing the outlet opening 90.

A possible system to extract the cassettes 10 from the stores is described below; the said system is envisaged for use with stores 9 arranged side by side with the respective outlet openings 90 all facing the same direction, in other words coplanar, and in the same way, with the respective access passages 91 facing the same direction, i.e. coplanar.

In this case the extraction means of the cassettes comprises first of all a base cursor, placed in the semi-space defined by the store access passages 91, not illustrated as this can be any mechanical element suitable for this purpose, activatable (by known means) in an alternative nearing and distancing sliding to and from the stores 9.

This base cursor extends along the row of stores 9 placed side by side.

Figure 16:
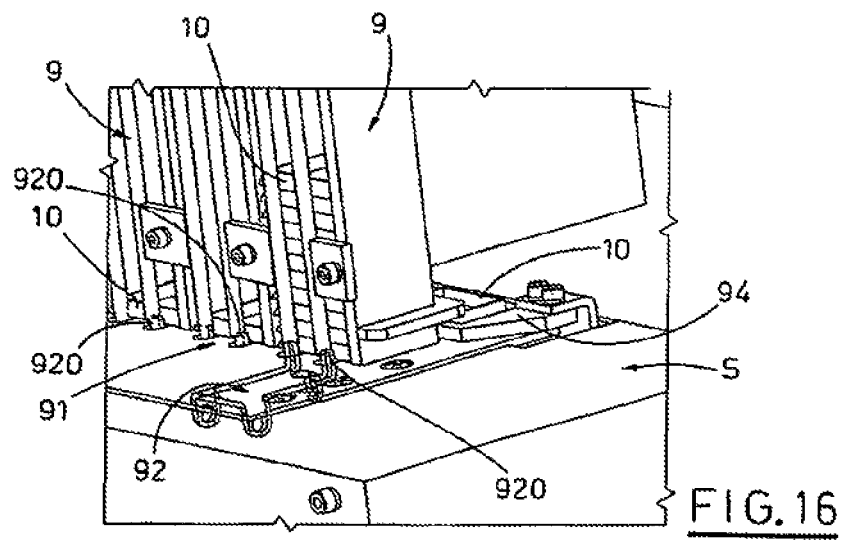
Figure 17:
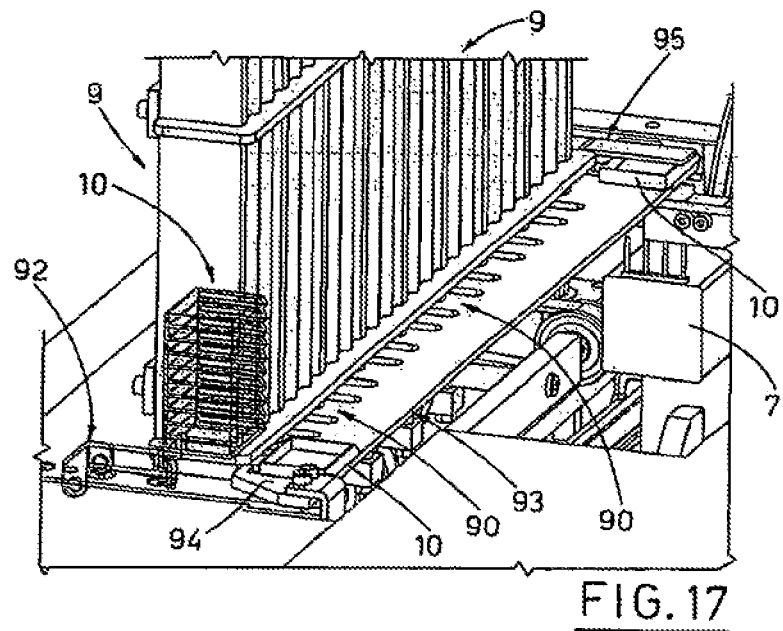

A plurality of pusher elements 92 (see FIG. 16 for example) are mounted on the base cursor, one for each access passage 91, each one arranged in front of the respective access passage 91.

Each pusher element 92, whose structure is detailed below, is mobile between an upper position in which it can insert itself in the respective access passage 91, upon sliding of the base cursor in the nearing direction to the stores 9, and a lower arrangement in which it passes freely below the rest base of the respective store 9, upon sliding of the base cursor in the nearing direction to the stores 9.

In practice the extraction of the cassettes 10 is as follows.

Once the store 9 from which the cassette 10 is to be extracted is selected, the relevant pusher element 92 is placed in the upper position, while the others remain in the lower one; the base cursor then slides towards the stores 9 and the pusher element 92 enters the passage 91 (the method is better described below), and pushes the cassette 10 which comes out through the outlet opening 90 and is transferred with the conveyor means 93, 94, 95 (described below).

In the meantime the other pusher elements 92 pass under the stores 9.

At this point the pusher element 92 returns to the lower position and the base cursor retracts away from the stores 9 (not necessarily in this order).

The pusher cursor 92 can essentially be in the shape of a plate, with one end hinged to the base cursor and the other end, the one facing the respective store 9, forming two or more tines 920 facing upwards, like horns.

When the said plate fitted with tines 920 is in the lower position, it can pass freely under the respective store, when it oscillates at the top, and therefore is in the upper position, the tines 920 can enter the access passage 91, and at the same time push the cassette 10 to the bottom and support the one right above, which in turn becomes the cassette at the bottom of the stack as soon as the tines 920 are lowered.

The actuator means of these invention components are known to experts in this sector.

With this extraction system the store 9 from which to extract the cassette 10 can always be defined as required, for example because each store houses cassettes of different types, for example of a different colour.

Other extraction systems can be conceived, in line with the concept of the invention, that foresee, in general, means to extract the cassettes 10 from the stores 9, that slide between a position which is distant from the store 9 and a position which is close, and which include a pusher element suitable to enter the access passage 91 of the stores 9.

Preferably, the conveyor means comprise an elongated plate 93 to slidably support an embedding cassette 10, arranged beside the row of stores 9 (but it can also work with one single store 9) with the respective sections along its length, positioned at the outlet openings 90 of the stores 9, so as to receive the cassette 10 resting on the base, pushed out from one of the stores 9.

The plate 93 is obviously used to receive the cassette 10 resting on its lower base 11.

The plate 93 also has an end nearer to the marking apparatus 1, for the transfer from the stores 9 to the apparatus 1.

The conveyor means also comprise a pusher slide 94, slidable on the plate 93, and having a pushing seat to engage the cassette 10, the slide 94 being activatable so as to push the cassette 10 along the plate 93 in the direction of the aforementioned end nearer to the marking apparatus 1.

In practice when a cassette 10 is pushed along the elongated plate 93, the slide is activated to take it to the marking apparatus 1.

The seat of the pusher slide is shaped so that it can receive and engage a part of the cassette 10, for example the rear part opposite the oblique surface 14, as shown in the example in the figures, and so as to prevent the cassette 10 from skidding while it slides resting on the elongated plate 93 (e.g. the seat can be "C" shaped).

When the cassette 10 reaches the end of the plate 93, it is preferably delivered to the marking apparatus by means of the transfer shuttle 95 described below. Before detailing the structure of the transfer shuttle 95, please note that, however it is made, it must comprise a housing suitable to releasably retain a cassette 10, and must also be movable between a position in which it is at the said end of the plate 93 nearer to the apparatus 1, whereby it is able to receive a cassette 10, and a position in which it is at the gripping pliers 31, 32, whereby it is able to deliver a cassette 10 thereto.

Preferably the transfer shuttle 95 comprises a lower plate 951 arranged flush to the end of the plate and able to receive a cassette 10, a limit switch 952 to detect the cassette 10 when it is pushed by the pusher slide 94 above the plate 951, and a stopper 950, which together with the plate 951, defines a "C" shaped seat suitable to releasably retain the cassette 10.

The transfer shuttle 95 can move horizontally in order to take the cassette 10 to the gripping pliers 31, 32, with the transfer shuttle 95 being at a height so that when shifted to the gripping pliers 31, 32, the latter, when in the aforementioned intermediate position, can close to grip the cassette 10 (see FIGS. 1, 2 and 18); at this stage the transfer shuttle 95 is retracted in the position in which its plate 951 is flush to the elongated plate 93.

A further advantageous feature is related to the expulsion or delivery phase of the marked cassette 10.

Considering that, as explained above, it is preferable to use gravity to make the marked cassette 10 drop out, then the outlet of the machine 100 is essentially defined by a slide 101.

The outlet 101 may be single with one slide or double with two slides; the outlet 1 or 2 can be selected using a program or can be ordered so that the cassettes are taken to an additional mechanical hand and arranged on a honeycomb-type container in chronological order.

In order to connect the gripping pliers 31, 32 to the slide 101, a flat element 35 can be mounted on the frame 5 of the gripping means, incorporated on the pliers 31, 32; the flat element 35 is arranged so as to receive the cassette 10 when the pliers 31, 32 are tilted in the above mentioned release position, and is configured so as to join onto the slide 101 in order to create together a continuous inclined surface, always when the pliers 31, 32 are in the release position.

It is understood that the above is described by way of a non-limiting example, therefore any construction variation is understood to be eligible for the same protection as the present technical solution, as outlined in the claims below.

The invention claimed is:

1. A marking apparatus for marking histology embedding cassettes, made of plastic material and being of a type comprising a flat base, a first and a second external side opposite one another, having respectively a first and a second surface perpendicular to the flat base and parallel to one another, and further comprising a third external side having a flat oblique surface, the apparatus being characterized in that it comprises:

at least a marking device suitable for marking plastic surfaces presented before it;

at least a gripping means able to alternatively grip and release an embedding cassette; and a movement organ to rotate the gripping means with respect to at least a first rotation axis (R) and at least a second rotation axis (Q):

the first rotation axis being arranged with respect to the gripping means in such a way that, in use, the first rotation axis is situated in an ideal plane that is parallel to and interposed between the ideal planes on which the perpendicular surfaces of a cassette gripped by the gripping means are located, so that, upon the rotation of the gripping means with respect to the first rotation axis, the first and the second perpendicular surfaces is alternatively located in front of the marking device the second rotation axis being perpendicular to the first rotation axis and being arranged with respect to he gripping means in such a way that, in use, upon the rotation of the gripping means with respect to the second rotation axis, the oblique surface of the gripped cassette is located in front.

2. The apparatus of claim 1, wherein the marking device is a laser marking device having an outlet for the laser emissions, which device is suitable for permanently marking surfaces of articles made of plastic material; the gripping means being arranged in front of the outlet of the marking device; and the first and second rotation axis being chosen such that, in use, upon rotations of the gripping means with respect to the first or the second rotation axis, the first perpendicular surface the second perpendicular surface and the oblique surface of a gripped cassette is alternatively arranged in front of the outlet of the marking device (2).

3. The apparatus of claim 2, , wherein the first and the second rotation axis of the movement organ are arranged with respect to one another in such a way that, upon rotations of the gripping means with respect to the first or the second rotation axis the first perpendicular surface, the second perpendicular surface and the oblique surface of a gripped cassette, is alternately arranged in a same ideal plane, facing the outlet of the marking device.

4. The apparatus of claim 1, wherein the gripping means comprises a gripping pliers having two jaws which are openable to receive one cassette at a time, and closable to grip the cassette the jaws being suitable to engage the flat base of the cassette and an upper portion thereof opposite the base, leaving the first and second perpendicular surfaces and the oblique surface thereof uncovered.

5. The apparatus of claim 4, wherein the laser marking device is arranged above the gripping pliers, which, upon rotations about the first rotation axis, is arrangeable alternately in an intermediate position in which the jaws of the pliers are one above another, so that in use a cassette when gripped is arranged horizontally, to first semi-tilted position in which the pliers is rotated by ninety degrees with respect to the intermediate position and in which the first perpendicular surface of the gripped cassette is directly facing the outlet (20) of the laser marking device, and a second semi-tilted position in which the pliers is rotated by one hundred eighty degrees with respect to the first semi-tilted position and in which the second perpendicular surface of the gripped cassette is horizontal and directly facing the outlet of the marking device; the pliers being further arrangeable, upon a rotation with respect to the second rotation axis, in a pitched position in which the gripped cassette is arranged obliquely with respect to the direction of gravity and the oblique surface thereof is horizontal and is directly facing the outlet of the marking device.

6. The apparatus of claim 1, wherein the movement organ comprises:

a first motor connectable to the gripping means and able to rotate the gripping means with respect to the first rotation axis, a support frame to which the gripping means are fixed, and a second motor connected to the support frame able to rotate the support frame with respect to the second rotation axis, whereby rotating the gripping means at the same time.

7. The apparatus of claim 6, wherein the movement organ further comprises a linear actuator connected to the gripping means and able to translate the gripping means in a vertical direction.

8. The apparatus of claim 6, wherein the frame is fixed rigidly to an end of a lever arm, the latter being hinged at another end thereof about the second rotation axis the arm being connected to said second motor so as to be activated thereby in rotation.

9. The machine of claim 8, wherein the conveyor means comprise at least an elongated plate to slidably support an embedding cassette, having as section located at the store and an end which is nearer the marking apparat, the conveyor means further comprising at least a pusher slide slidable on the plate, and having a pushing seating to engage a cassette, the slide being activatable so as to push the cassette along the plate in the direction of the nearer end thereof to the marking apparatus.

10. The machine of claim 9, wherein the conveyor means comprise a transfer shuttle to displace an embedding cassette from the plate to the marking apparatus, the shuttle comprising a housing suitable to releasbly retain a cassette, and further being movable between a position in which it is at said nearer end of the Plate, whereby it is able to receive a cassette, and a position in which it is at the gripping means, whereby it able to deliver a cassette thereto.

11. A machine for supplying already-marked histology embedding cassettes, comprising:

at least a marking apparatus according to claim 1, at least a store to retain a multiplicity of embedding cassettes;

conveyor means to supply one cassette at a time to the marking apparatus arranged between the store and the marking apparatus; and at least an outlet to provide an operator with a marked histology embedding cassette.

12. The machine of claim 11, wherein the store is able to contain a vertical stack of cassettes so that the latter can vertically slide in the store, a lower rest base to support the stack of cassettes, the store further comprising an outlet opening arranged at the base, which in use faces directly a cassette that rests directly on the base, and has site which is sufficient for passage of a cassette, the store further having an access passage (91), which is opposite the outlet opening, by means of which the cassette is directly accessible from outside.

13. The machine of claim 12, comprising extraction means of the cassettes from the store, slidable between a more distant position from the store and a closer position thereto, and comprising a pusher element able to insert in the access passage of the store.

14. The machine of claim 13, comprising a plurality of vertical stores arranged side by side with the respective outlet openings al1 facing in a same direction, wherein the extracting means of the cassettes comprise a base cursor, activatable in an alternative nearing and distancing sliding to and from the stores, a pusher element being mounted to the base cursor for each access passage of the stores, each pusher element being mobile between an upper position in which it can insert itself in the respective access passage, upon the sliding of the base cursor in the nearing direction to the stores, and a lower arrangement in which it passes freely below the rest base of the respective store, upon the sliding of the base cursor in the nearing direction to the stores.

* * * * *